US 7,584,646 B2

(12) United States Patent
Schleif et al.

(10) Patent No.: US 7,584,646 B2
(45) Date of Patent: Sep. 8, 2009

(54) DEVICE FOR MEASURING COEFFICIENT OF FRICTION

(75) Inventors: Kurt Kramer Schleif, Dearborn, MI (US); Brian B. Wampler, Clinton Township, MI (US); Timothy J. Kapelanski, Plymouth, MI (US); Bruce Whittle, Plymouth, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 174 days.

(21) Appl. No.: 11/517,273

(22) Filed: Sep. 8, 2006

(65) Prior Publication Data
US 2008/0060411 A1    Mar. 13, 2008

(51) Int. Cl.
*G01N 19/02* (2006.01)
(52) U.S. Cl. .............................. 73/9; 73/146
(58) Field of Classification Search ......... 73/9, 73/117.02, 146, 10; *E01C 23/00*
See application file for complete search history.

(56) References Cited

U.S. PATENT DOCUMENTS

| 2,225,140 | A |   | 12/1940 | Walker |
| 3,301,039 | A |   | 1/1967  | Kummer |
| 4,145,028 | A | * | 3/1979  | Kelley et al. ............... 254/346 |
| 4,187,714 | A |   | 2/1980  | Cox et al. |
| 4,694,690 | A | * | 9/1987  | Jones et al. .................... 73/146 |
| 4,813,266 | A | * | 3/1989  | Nash ............................... 73/9 |
| 4,895,015 | A |   | 1/1990  | English |
| 5,060,965 | A | * | 10/1991 | Haefner et al. ............... 280/504 |
| 5,245,856 | A | * | 9/1993  | Pazzaglia et al. ................. 73/9 |
| 5,501,097 | A |   | 3/1996  | Nomura |
| 5,736,630 | A |   | 4/1998  | Welner |
| 5,743,784 | A | * | 4/1998  | Birang et al. .................. 451/21 |
| 5,753,823 | A | * | 5/1998  | Chang et al. .................. 73/842 |
| 5,777,240 | A | * | 7/1998  | Lefebvre et al. ........ 73/862.634 |
| 6,923,038 | B2 |  | 8/2005  | Klovning |
| 6,928,857 | B1 |  | 8/2005  | Brown |
| 7,338,718 | B2 | * | 3/2008 | Taira et al. ................... 428/633 |
| 7,373,101 | B2 | * | 5/2008 | Hozumi et al. ............... 399/346 |
| 2002/0126922 | A1 | * | 9/2002 | Cheng et al. .................... 384/1 |
| 2004/0116309 | A1 | * | 6/2004 | Yokota et al. ................ 508/463 |

OTHER PUBLICATIONS

SAFE Dragsled located at http://ridders.com/news_94.html visited on Jun. 23, 2006. (11 pages).

* cited by examiner

*Primary Examiner*—Thomas P Noland
(74) *Attorney, Agent, or Firm*—O'Brien Jones, PLLC

(57) ABSTRACT

A device for measuring the coefficient of friction between a test surface and a test material, comprising a frame, a skid pad comprising the test material and attached to an underside of the frame to contact the test surface, a longitudinal force measuring device attached to the frame and having an axis, and a longitudinal pulling assembly exerting a longitudinal pulling force on the drag sled and the longitudinal force measuring device. The longitudinal force measuring device is capable of outputting data indicative of the longitudinal force applied to the device. The longitudinal pulling force is vertically aligned with the axis of the longitudinal force measuring device.

17 Claims, 7 Drawing Sheets

DEVICE FOR MEASURING COEFFICIENT OF FRICTION

FIELD OF INVENTION

This invention relates to the field of friction measurement. More specifically, this invention relates to a device for measuring the coefficient of friction between a test surface and a material or representative material.

BACKGROUND

The coefficient of friction is the ratio of the friction force to the normal force. There are several known methods to measure the coefficient of friction. The Horizontal Pull Slipmeter ("HPS") consists of two basic elements: (1) a drag sled mounted on slider feet and equipped with a force gauge, and (2) a device for pulling the sled at a controlled rate of speed across the surface being tested. Another device, described in U.S. Pat. No. 4,895,015, is an improvement to the HPS that utilizes a drag sled and a stationary pulling mechanism with a set of guide tracks. The drag sled is pulled by a motor and guided along the tracks, which assure alignment of the pull. The force required to pull the drag sled is measured, thus allowing a determination of the coefficient of friction.

Another device, described in U.S. Pat. No. 4,813,266, consists of a test block connected to a microprocessor. The bottom of the test block is covered with a material for which the coefficient of friction will be measured. The test block is set on a test surface and the block is given an impulse with a hammer or other object. The impulse causes the block to move along the surface. An accelerometer on the test block transmits acceleration data to the microprocessor. The acceleration data includes information on the acceleration of the block caused by the impulse and the deceleration of the block as it comes to a stop after the impulse. This acceleration data is used by the microprocessor to determine the coefficient of friction at a specific point on the test surface.

In laboratories, tire testing machines typically use an expendable material such as 80-grit sandpaper to simulate a roadway surface. As tests are conducted, the aggregate of the sandpaper begins to wear and degrade, resulting in a less abrasive simulated roadway surface. This can jeopardize the test data.

In most cases it is desirable, but impractical, to maintain a constant coefficient of friction between the tire and the roadway surface. To prevent testing of a tire on an overly worn or inconsistent surface, the laboratory operator must monitor surface degradation of the sandpaper. It is known to monitor surface degradation visually or by running a hand over the width of the sandpaper surface, feeling for a change in surface roughness. When significant variation is felt across various points on the surface, the sandpaper is considered "worn," and should be replaced. New sandpaper is applied for further equipment testing.

This method of monitoring sandpaper surface wear can be problematic because it is based on a subjective evaluation of the sandpaper surface roughness, which is not sufficient because it is highly operator-dependant and can result in two error modes: (1) prematurely changing the sandpaper, which is labor intensive and increases costs; or (2) conducting sensitive tire testing on a non-representative (worn) sandpaper surface. A sandpaper surface can, for example, cost $200 and removal/replacement can take 6-8 hours of technician time. Data collected for a worn sandpaper surface can jeopardize computer models.

A quantitative method is needed in which the coefficient of friction is measured and tracked for improve data integrity.

BRIEF SUMMARY OF THE INVENTION

In one embodiment, the invention is directed to a device for measuring the coefficient of friction between a test surface and a test material, comprising a frame, a skid pad comprising the test material and attached to an underside of the frame to contact the test surface, a longitudinal force measuring device attached to the frame and having an axis, and a longitudinal pulling assembly exerting a longitudinal pulling force on the drag sled and the longitudinal force measuring device. The longitudinal force measuring device is capable of outputting data indicative of the longitudinal force applied to the device. The longitudinal pulling force is vertically and laterally aligned with the axis of the longitudinal force measuring device.

In another embodiment, the invention is directed to a method for measuring the coefficient of friction between a test surface and a test material that comprises providing a friction measuring device including a skid pad comprising the test material and attached to an underside of a frame to contact the test surface, the friction measuring device also including a longitudinal force measuring device and a longitudinal pulling assembly attached to the longitudinal force measuring device; applying a longitudinal force with the pulling assembly to move the friction measuring device relative to the test surface, such that the axis of the longitudinal force is vertically and laterally aligned with a vertical center of mass $CM_V$ of the device and an axis of the longitudinal force measuring device; and outputting data indicative of the longitudinal force applied to the friction measuring device.

In yet another embodiment, the invention is directed to a device for measuring the coefficient of friction between a test surface and a test material, comprising a frame, a skid pad comprising the test material and attached to an underside of the frame to contact the test surface, a longitudinal force measuring device attached to the frame and having an axis, and a longitudinal pulling assembly exerting a longitudinal pulling force on the drag sled through the longitudinal force measuring device. The longitudinal force measuring device being capable of outputting data indicative of the longitudinal force applied to the device. The longitudinal pulling force is horizontally aligned with the axis of the of the longitudinal force measuring device.

Further features of the present invention, as well as the structure of various embodiments of the present invention are described in detail below with reference to the accompanying drawings.

BRIEF DESCRIPTION OF THE DRAWINGS

The accompanying drawings, which are incorporated herein and form part of the specification, illustrate the present invention and together with the description, further serve to explain the principles of the invention and to enable a person skilled in the pertinent art to make and use the invention. In the drawings, like reference numbers indicate identical or functionally similar elements.

DETAILED DESCRIPTION OF THE INVENTION

Figure 1:
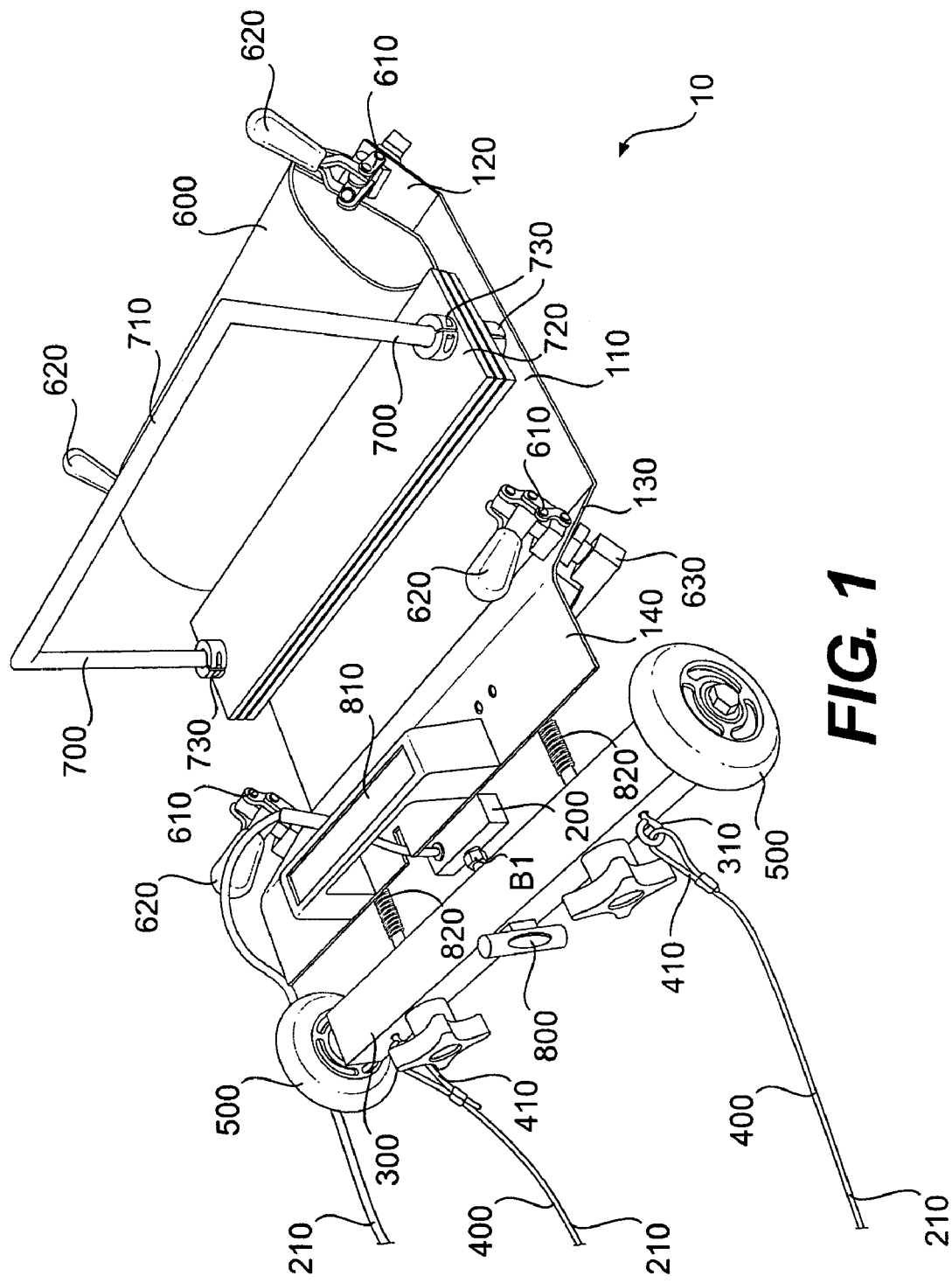
FIG. 1 is a perspective view of a drag sled in accordance with an embodiment of the invention.

A drag sled device was designed to quantify the coefficient of friction between a test surface and a representative material. For example, the test surface can be an 80-grit sandpaper in a dynamic tire test machine such as a Flat Trac® test machine. Sensitive tire performance data can be acquired on the Flat Trac® test machine, which is a tire test machine having a sandpaper test surface applied to a roadway similar to that of a belt sander—wherein a tire is applied to the sandpaper surface to test vehicle dynamics handling, rollover prediction, J-turn analysis, fishhook testing, lateral sweeps, etc . . . The performance data acquired on the Flat Trac® test machine should be of the highest quality. Inaccurate data resulting from a worn sandpaper surface can result in poor CAE simulations. A CAE simulation takes data from the Flat Trac® test machine and plugs it into data analysis software to simulate J-turn, fishhook testing, etc.

In this example, the drag sled is placed on the sandpaper surface of the Flat Trac® test machine and held stationary while the sandpaper surface moves as in normal operation, which allows the drag sled to measure peak/static/breakaway friction and/or sliding/dynamic/kinetic friction. The friction measurements can optionally be tracked using Statistical Process Control (SPC) charts, which provide a method for tracking and monitoring output representing changes in processes to see how output varies over time according to a number of rules. Adherence to one of the rules ensures that the process is in control. The SPC techniques allow a laboratory to determine the exact point in time when the sandpaper surface needs to be replaced. In an embodiment of the invention, a Six Sigma control methodology is used.

The drag sled quantifies the coefficient of friction using the equation $F=\mu N$, where F is the longitudinal force required to pull the drag sled, $\mu$ is the coefficient of friction, and N is the normal force or weight of the drag sled. The drag sled is made to move relative to a substantially horizontal test surface. A load cell measures the longitudinal force F required to move the drag sled relative to the test surface. The drag sled is then removed from the test surface and hung vertically from a hook. Hanging the drag sled allows the drag sled's weight N to be measured. From these two measurements, the coefficient of friction $\mu$ can be calculated.

In addition to use with a dynamic tire test machine such as a Flat Trac® test machine, the drag sled of the present invention can be used with a Rolling Resistance tire machine, which uses a large drum with a curved surface to measure tire performance. The drag sled for use in this application would have an arcuate skid pad shape that complements the curved surface of the drum.

The present invention also contemplates using the drag sled to improve measurements used in (1) proving grounds to measure roadway coefficient of friction, (2) raceways for evaluating track conditions, (3) automobile accident reconstruction and forensics, (4) airport runway evaluations, and (5) slip and fall accident investigations. In these applications, the drag sled is pulled over the surface to measure the coefficient of friction, rather than being held stationary while a sandpaper surface moves to determine whether the sandpaper surface is worn.

The present invention monitors proving ground surfaces (Vehicle Dynamic Area (VDA) pads) by monitoring changes in surface friction of asphalt, concrete, or other roadway surfaces, thus eliminating the need for expensive traction trailers. The present invention can also be used to compare proving ground surfaces so that desirable surfaces can be replicated.

FIG. 1 is a perspective view of a drag sled device 10 in accordance with an embodiment of the invention. A sled body or frame 100 (see FIG. 4) has a main portion 110, an inclined portion 120 to the rear, and an inclined portion 130 to the front that extends from the main portion 110 to an optional ridge 140. The ridge 140 can overlie a longitudinal force measuring device such as a load cell 200, which will be described below with reference to FIG. 3.

At the front of the device 10 is a stabilizer bar 300 that preferably spans substantially the entire width of the device 10. The stabilizer bar 300 can include a variety of cross-sectional shapes, including square (as shown), triangular, circular, I-shaped, etc. The stabilizer bar 300 can be made of any suitably strong material, and should be as light as feasible. For example, steel, aluminum, or carbon fiber can be used. The stabilizer bar 300 is connected to a longitudinal pulling assembly including a pull cable 400 on a side of the stabilizer bar 300 that is opposite the frame 100. The pull cable 400 is used to pull the drag sled 10, and can be attached to the stabilizer bar 300 using loops 410 threaded through eye bolts 310. The stabilizer bar 300 transmits a load from the pull cable 400 to the load cell 200 with minimal lateral or vertical moments, which is accomplished as described in more detail below. A load cell 200 is an instrument capable of measuring the longitudinal force applied to the sled body via the pulling assembly and the stabilizer bar 300.

The stabilizer bar 300 is supported on both ends with wheels 500 that can be polyurethane and can, for example, be readily available wheels used for in-line skating. The wheels should add minimal friction to the drag sled so that virtually all of the friction is created by the skid pad's contact with the test surface. In an embodiment of the invention, to minimize pitch, the wheels 500 are sized to support the stabilizer bar 300 at such a vertical height that the axis of the load cell 200 is located at the same vertical height above the test surface as the sled's vertical center of mass $CM_V$ and the load path of the pulling force applied by the pulling assembly.

Figure 2:
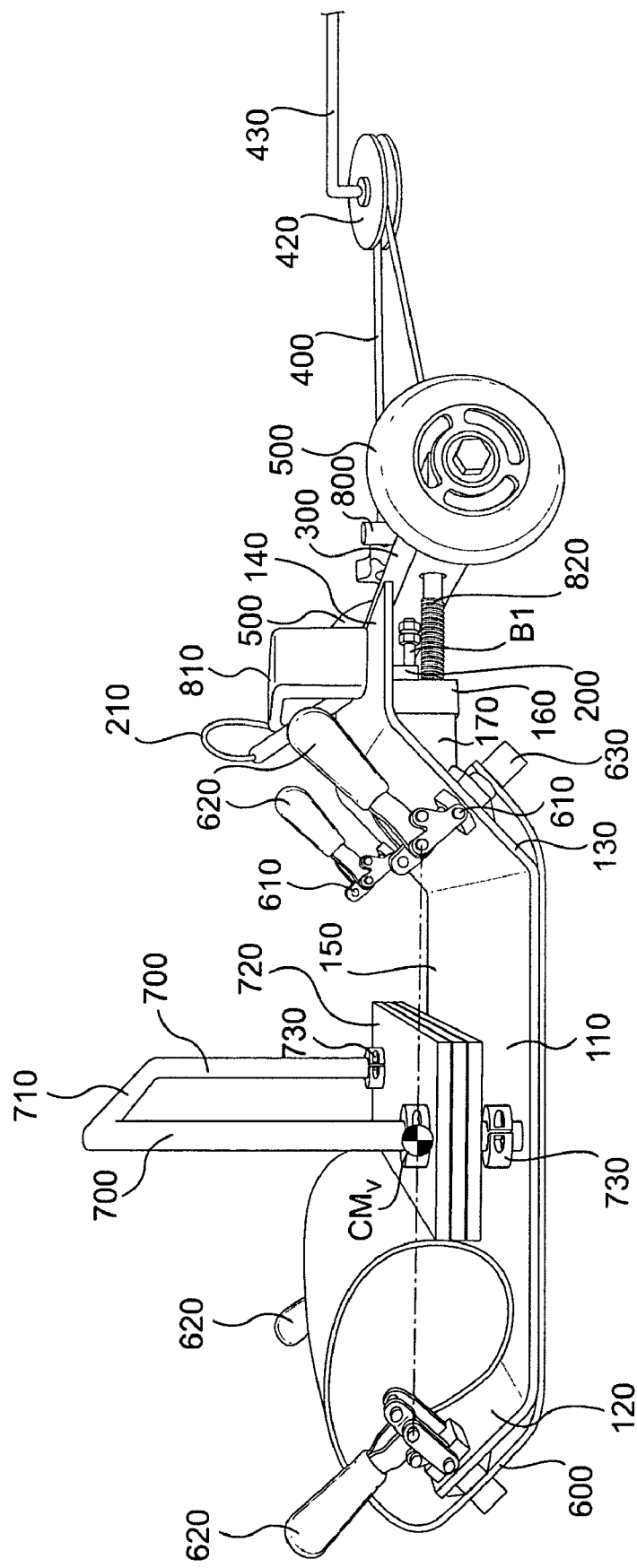
FIG. 2 is a side view of the drag sled embodiment of FIG. 1.
Figure 6:
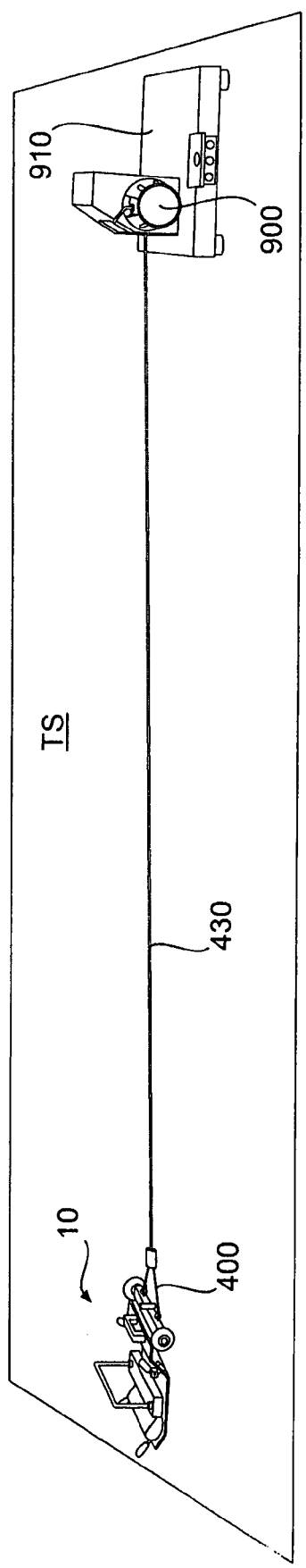
FIG. 6 illustrates a system including a winch for pulling a drag sled in accordance with an embodiment of the invention.

As shown in FIG. 2, a skid pad 600 runs along the underside of the sled frame 100. The skid pad 600 comprises a sheet of material being evaluated, or a sheet that represents a material being evaluated, and may comprise a rubber compound or polyurethane. The skid pad 600 and the wheels 500 are preferably the only components of the sled that are in contact with the test surface TS (see FIG. 6). The skid pad 600 need not span the entire width of the frame 100. The skid pad thickness may vary, but should be coordinated with the wheel height to align the vertical center of mass $CM_V$ of the sled with the load cell's axis and the load path of the pulling force applied by the pulling assembly. The skid pad typically comprises a ⅛ inch thick sheet. In the embodiment illustrated, the skid pad 600 is held tightly in place under the frame 100 using an attachment system such as toggle clamps 610 having handles 620. As illustrated, four toggle clamps 610 can be used to suitably secure the skid pad 600 in tension to the frame 100, one being located in each corner of the frame 100. The toggle clamps 610 are mounted so that, in operation, they do not touch the surface on which the drag sled device 10 slides. The attachment system may also include clamp bars 630 extending between and tightened via the toggle clamps 620 along the underside of each inclined portion 120, 130 to apply a generally uniform pressure across the width of the drag sled 10 to hold the skid pad in place. Other suitable fastening means, preferably removable, can alternatively or additionally be used to secure the skid pad 600 to the frame 100.

The device may also include, on a top side 150 (see FIG. 2) of the main portion 110 of the frame 100, a system for adjusting the drag sled's vertical center of mass $CM_V$. The system can include, for example, two uprights 700 and a connecting cross member 710. The uprights 700 are mounted to the frame 100 either removably (e.g., via bolts) or fixedly (e.g., via welding). In an embodiment of the invention, the uprights comprise a 7/16" diameter tube made from a metal such as steel. One way to attach the upright is to thread a portion of each upright 700 and mate that portion with a bolt 715 (see FIG. 7) inserted from a bottom side of frame 100. The uprights 700 allow the addition of ballast weight 720 to the device 10, which can increase the overall weight of the device 10 and be adjusted vertically to adjust the device's vertical center of mass $CM_V$ as needed to align the vertical center of mass $CM_V$ with the longitudinal load path and the axis of the load cell 200. The amount of ballast weight 720 can be adjusted based on the weight of the sled 10, the composition of the skid pad 600, and the macrotexture of test surface TS. More weight is generally used for a more aggressive surface. To adjust the device's vertical center of mass $CM_V$, the ballast weight 720 can be adjusted vertically along the uprights 700 to align the vertical center of mass $CM_V$ with the longitudinal load path and the axis of the load cell 200. Stop collars 730 can be used to retain the ballast 720 in a raised position. In an exemplary embodiment, a drag sled device 10 may weigh about 12 pounds and have a ballast weight 720 of about 13 pounds.

An embodiment of the invention may further comprise a level 800 mounted on the stabilizer bar 300. The level 800 assists the operator in aligning (vertically) the load cell's axis with the drag sled's vertical center of mass $CM_V$ and the load path of the pulling force applied by the pulling assembly, in an effort to reduce or eliminate the vertical moment (or "pitch") effecting measurements taken by the load cell 200. The device 10 may also include a handle 810 attached to the sled frame 100 to enable easy handling of the device. Another optional feature of the invention is one or more removable load cell protection pins 820 that preferably extend through the stabilizer bar 300 to protect the load cell 200 from damage by preventing the stabilizer bar 300 from moving relative to the load cell 200 when the device is not in use. For the load cell 200 to operate properly, the load cell protection pins 820 must be removed before the device is used. The pins 820 can be retained by bolts 830 that are preferably mounted beneath the ridge portion 140 of the frame 100 (see FIG. 3).

Figure 3:
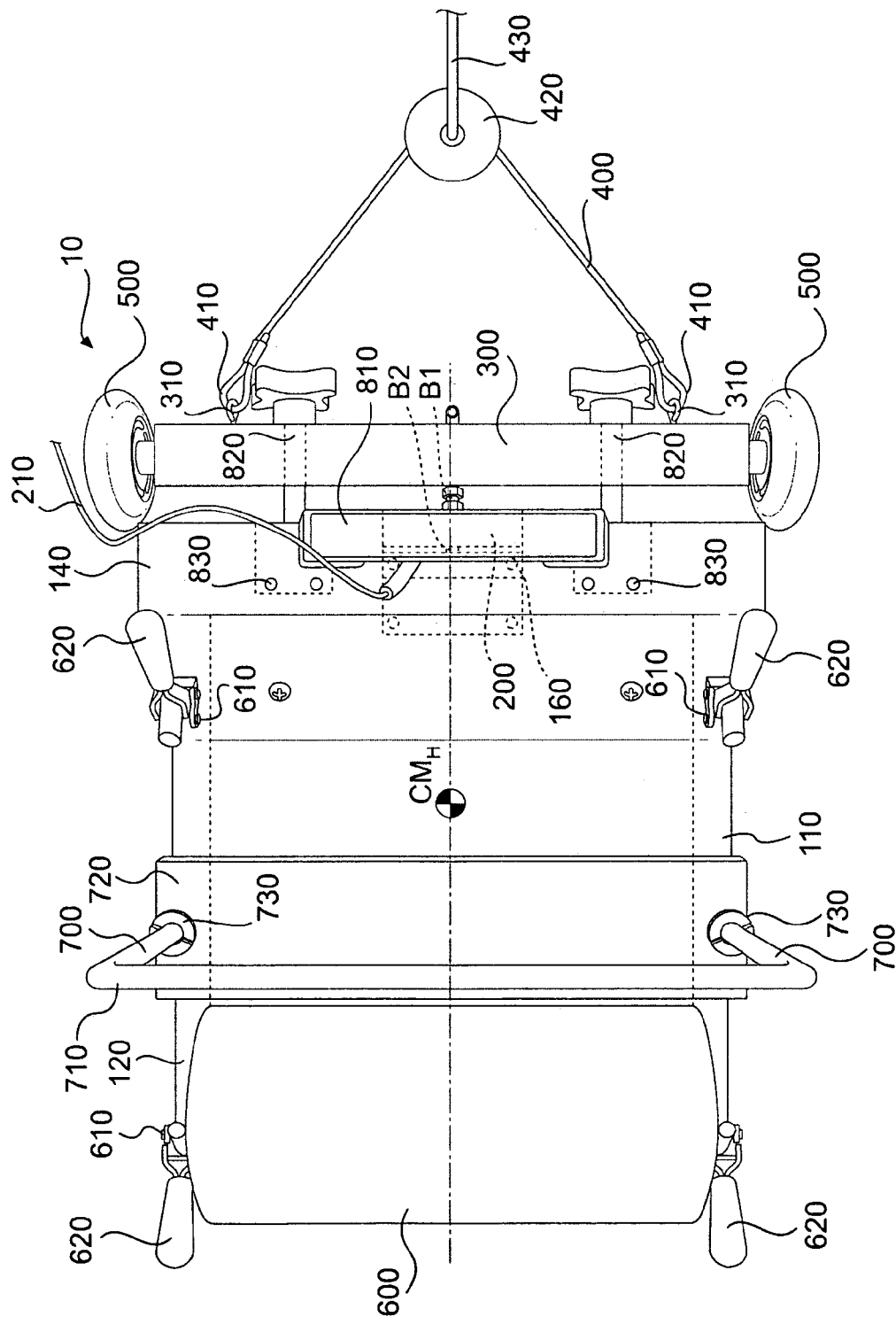
FIG. 3 is a top view of the drag sled embodiment of FIG. 1.
Figure 7:
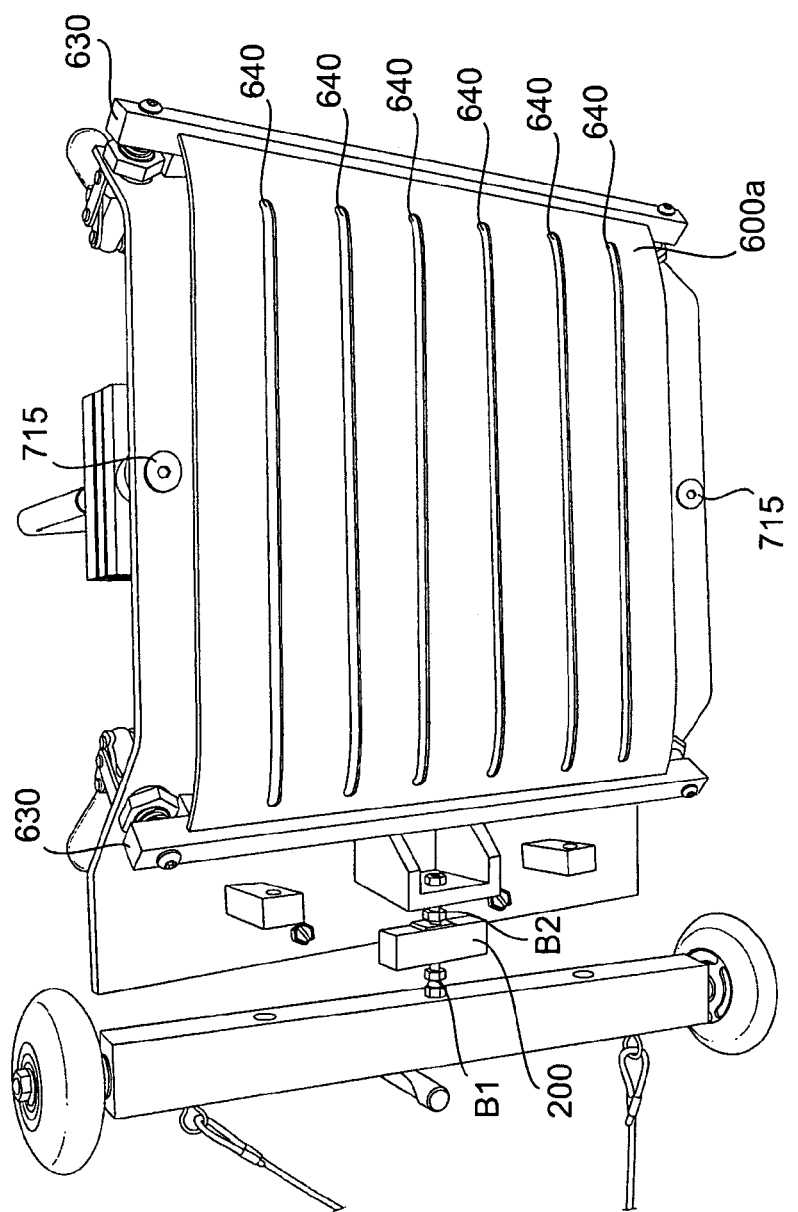
FIG. 7 illustrates another embodiment of a skid pad for use in the present invention.

FIG. 2 is a side view of the drag sled embodiment of FIG. 1. FIG. 3 illustrates a top view of an embodiment of the drag sled device 10. These Figures, along with FIG. 7, illustrate an exemplary embodiment for attaching the load cell 200 to the frame 100. As can be seen, the load cell 200 is connected to the stabilizer bar 300 via a bolt B1 such that a pulling force applied to the stabilizer bar 300 is also applied to the load cell 200. Another bolt B2 extends from the load cell 200 to a mounting bracket 160. Thus, the load cell 200 is suspended between the two bolts B1, B2. The mounting bracket 160 can be mounted to the overlying ridge 140 of the drag sled frame 100. A gusset 170 may be used to reinforce the joint where the mounting bracket 160 and the ridge 140 meet.

Figure 4:
FIG. 4 is a side view of an embodiment of the drag sled frame.
Figure 5:
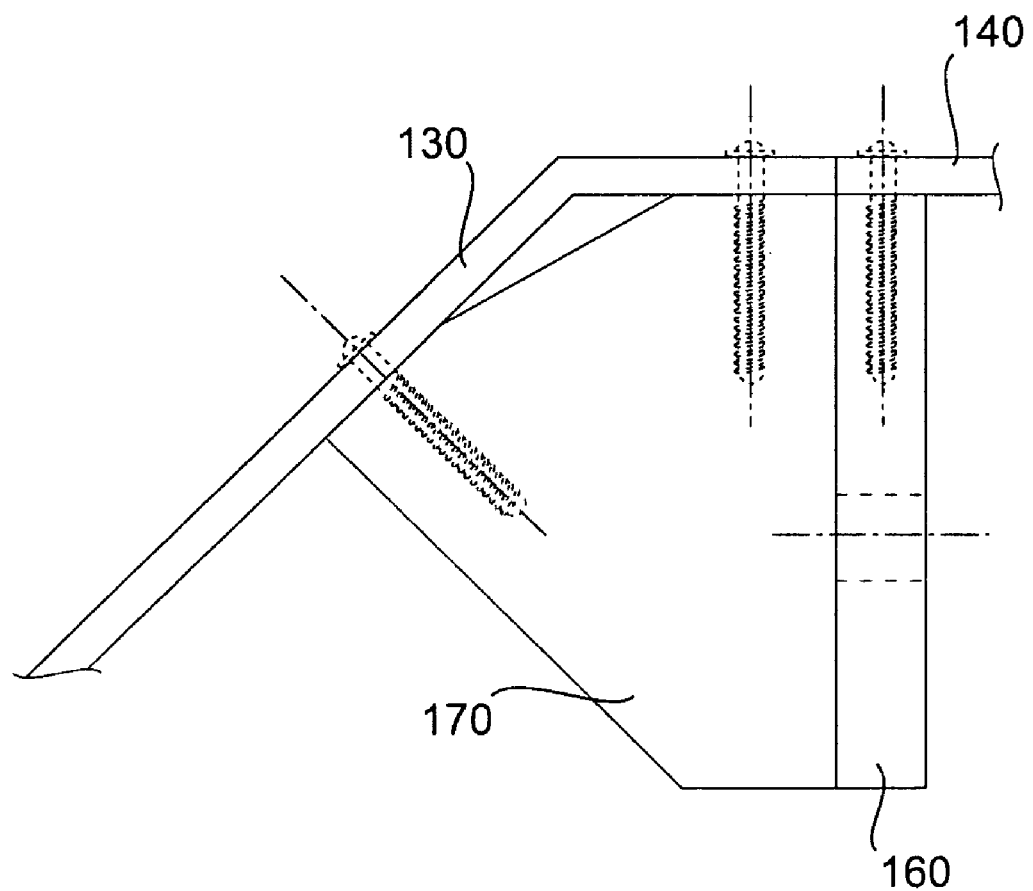
FIG. 5 illustrates attachment of an embodiment of the drag sled frame to a mounting plate and gusset.

FIG. 4 is a side view of an embodiment of the drag sled frame 100 illustrating that the inclined portions 120, 130 may be inclined at a 45° angle from main portion 100. The ridge 140 is preferably parallel to the main portion 110. FIG. 5 illustrates attachment of the drag sled frame 100 to the mounting bracket 160 and gusset 170. The gusset 170 and mounting bracket 160 may be removably or fixedly attached to the frame 100 via known techniques such as screws, as shown, or welding.

To minimize vertical and horizontal moments, or pitch and yaw, respectively, the vertical offset between the axis of the load cell 200, the vertical center of mass $CM_V$ of the sled, and the load path of the pulling force should be minimized. As stated above, the vertical center of mass $CM_V$ of the sled 10 is adjusted by adjusting the ballast weight 720 vertically on the uprights 700. One way to do this is to hang the sled by its pull cable 400, and then adjust the ballast weight 720 on the uprights 700 to be sure the sled hangs completely vertically. The level 800 assists the operator in ensuring that the sled 10 hangs vertically. Horizontal moment, or yaw, is minimized by spacing the eye bolts 310 equal distances from the center of the stabilizer bar 300, which should be aligned with the load cell's axis and preferably additionally the drag sled's horizontal center of mass $CM_H$. In addition, the longitudinal pulling assembly can utilize a pulley 420 with the pull cable 400 extending therethrough, as illustrated, to ensure equal pulling forces on the eye bolts 310 to further minimize yaw. The pulley 420 also allows the drag sled 10 to center itself and steer at a zero degree heading. A clevis (not shown) may be used instead of, or in addition to, the pulley. The pulley 420 and optional clevis allow a longitudinal pull force to be applied evenly to the pull cable 400. When in equilibrium, the pulley creates uniform tension throughout the pull cable 400.

The pulley 420 can be attached to either a Flat Trac® test machine or a pull system such as a winch. An exemplary embodiment of a suitable winch 900 on a portable platform 910 is illustrated in FIG. 7. The winch 900 is preferably portable to enable easy relocation to areas, such as proving grounds, tracks, and runways that are to be tested with the drag sled 10.

The winch 900 is preferably positioned so that the cables 400, 430 are horizontal and parallel to the test surface when in tension. An exemplary winch suitable for use with a drag sled of the present invention includes a Warn 9.5ti Thermometric Self-Recovery Winch. In an embodiment of the invention, to prevent oscillation from effecting measurements obtained from the winch-sled system, a tow cable 430 between the winch 900 and the sled 10 should be light weight, but be thick enough to have substantially no stretch in use. For example, a steel braided cable having a ⅛" thickness can be used. In addition, the tow cable 430 is preferably not coated with a material that allows it to stretch in use. Further, the length of the tow cable 430 should be chosen to minimize stretching and minimize the affects of external forces (such as wind) during testing. For example, a tow cable 430 having a length of about 30 feet may be used. Still further, to prevent oscillation from affecting measurements, the pulley 420 is preferably light-weight. When used according to an embodiment of the invention to measure dynamic friction, the winch 900 should be capable of pulling the drag sled 10 at a constant rate of speed of about one foot per second, so that slide sticking can be prevented and the drag sled can be kept in a pure sliding mode.

When used with a dynamic tire test machine such as a Flat Trac® tire test machine, the drag sled 10 of the present invention remains stationary relative to the test machine as the test machine's sandpaper surface moves. According to an embodiment of the invention, the drag sled 10 remains stationary by routing the pull cable 400 through a pulley 420 that is attached to a stationary part of the Flat Trac® tire test machine or to an object that is stationary relative to the Flat Trac® tire test machine.

In some cases, improved dynamic friction measurements can be obtained by allowing the drag sled to drag across the test surface for about five feet before beginning measurement.

Data is output from the drag sled 10 to a data acquisition system via, for example, a two-wire signal output 210 that is standard with the load cell 200. The load cell may be, for example, an Interface model SML Series. The data acquisition system should be capable of receiving data from the type of load cell used, and may include a digital readout that displays the coefficient of friction. Alternatively, the data can be output to device with tracking software, or to a Flat Trac® tire test machine.

FIG. 7 illustrates an alternative embodiment of the skid pad of the present invention, which may be used when testing wet surfaces. As illustrated, the skid pad 600a includes one or more sipes 640 that channel water, thereby reducing the potential for the test results being affected by hydroplaning or vacuum suction of the skid pad. The sipes 640 may be spaced, for example, about 1.5 inches apart. The sipes 640 need not extend along the entire length of the drag sled, but preferably extend along the length of the drag sled that contacts the ground during testing. The number and size of the sipes can vary greatly while still adequately lowering the effects of hydroplaning or vacuum suction on friction measurement.

When using the drag sled for wet testing, because many materials used for the skid pad may absorb water, the operator may place the drag sled on the wet test surface and allow ample time for the skid pad to soak and absorb water until saturated prior to testing.

To use the drag sled outdoors for testing such as proving ground testing, the drag sled and pull system should be arranged so that any wind is blowing longitudinally relative to the drag sled. Cross-wind setups should be avoided when possible, so that tow cable oscillation can be minimized. Debris should be removed from the test surface and any other surfaces the drag sled may be subjected to. The cleaning process can be repeated as necessary to ensure that the test surface remains free of debris. The drag sled is placed in its starting position and the load cell protection pins, if available, are removed. The winch can then be positioned in its appropriate position which may be, for example, about thirty feet from the drag sled.

After the winch and drag sled are positioned properly, the winch's tow cable is extended until it reaches the drag sled. The tow cable is then connected to the pulley that is looped through the pull cable. The tow cable can be secured to the pulley using a clevis and a cotter pin. The load cell can then be connected to the data acquisition system. The load cell should be zeroed before use. A remote control may be used to turn the winch on/off.

What is claimed is:

1. A drag device for measuring the coefficient of friction between a test surface and a test material, comprising:
   a frame;
   a skid pad comprising the test material and attached to an underside of the frame to contact the test surface;
   a system for adjusting the center of mass of the device;
   a longitudinal force measuring device attached to the frame and having an axis, the longitudinal force measuring device being capable of outputting data indicative of the longitudinal force applied to the drag device; and
   a longitudinal pulling assembly exerting a longitudinal pulling force on the drag device and the longitudinal force measuring device,
   wherein the longitudinal pulling force is vertically aligned with the axis of the longitudinal force measuring device.

2. The device of claim 1, wherein the center of mass of the drag device is vertically aligned with the axis of the longitudinal force measuring device.

3. The device of claim 1, wherein the skid pad test material comprises one of a rubber compound and polyurethane.

4. The device of claim 1, wherein the system for adjusting the center of mass of the device comprises uprights and a ballast weight.

5. The device of claim 4, wherein the system for adjusting the center of mass of the drag device further comprises a level attached thereto.

6. The device of claim 1, further comprising a stabilizer bar between the longitudinal force measuring device and the longitudinal pulling assembly.

7. The device of claim 6, wherein the longitudinal pulling assembly comprises a pull cable extending through a pulley, the pull cable being attached to the stabilizer bar such that the longitudinal pulling force is applied to the longitudinal force measuring device though the stabilizer bar.

8. The device of claim 1, further comprising an attachment system for attaching the skid pad to the underside of the frame, the attachment system comprising toggle clamps.

9. The device of claim 8, wherein the attachment system further comprises clamp bars extending between adjacent toggle clamps.

10. The device of claim 1, wherein the drag device is attached to a pull system.

11. The device of claim 10, wherein the pull system includes a winch and a tow cable.

12. A drag device for measuring the coefficient of friction between a test surface and a test material, comprising:
    a frame;
    a skid pad comprising the test material and attached to an underside of the frame to contact the test surface;
    a load cell attached to the frame and having an axis, the load cell being capable of outputting data indicative of the longitudinal force applied to the drag device;
    protection pins that protect the load cell from damage when the device is not in use; and
    a longitudinal pulling assembly exerting a longitudinal pulling force on the drag device and the load cell,
    wherein the longitudinal pulling force is vertically aligned with the axis of the load cell.

13. A method for measuring the coefficient of friction between a test surface and a test material, the method comprising:
    providing a friction measuring device including a skid pad comprising the test material and attached to an underside of a frame to contact the test surface, the friction measuring device also including a longitudinal force measuring device and a longitudinal pulling assembly attached to the longitudinal force measuring device;
    applying a longitudinal force with the pulling assembly to move the friction measuring device relative to the test surface, such that the load path of the longitudinal force is vertically aligned with a center of mass of the friction measuring device and an axis of the longitudinal force measuring device; and
    outputting data indicative of the longitudinal force applied to the friction measuring device,
    wherein the friction measuring device is used with a dynamic tire test machine, and the longitudinal force is applied to prevent movement of the friction measuring device relative to a test surface of the dynamic tire test machine, and wherein the test surface of the dynamic tire test machine is a sandpaper surface, and the friction measuring device is configured to determine when the sandpaper surface has become worn or inconsistent and should be replaced.

14. The method of claim 13, wherein the friction measuring device moves relative to the test surface at a speed to prevent slide sticking and keep the friction measuring device in a sliding mode to measure dynamic friction.

15. The method of claim 13, wherein the test surface is one of a proving ground, a race track, a roadway, and an airport runway, and the friction measuring device is pulled across the test surface to monitor one of a static friction and a dynamic friction.

16. A drag device for measuring the coefficient of friction between a test surface and a test material, comprising:
   a frame;
   a skid pad comprising the test material and attached to an underside of the frame to contact the test surface;
   a system for adjusting the center of mass of the drag device;
   a longitudinal force measuring device attached to the frame and having an axis, the longitudinal force measuring device being capable of outputting data indicative of the longitudinal force applied to the drag device; and
   a longitudinal pulling assembly exerting a longitudinal pulling force on the drag sled through the longitudinal force measuring device,
   wherein the longitudinal pulling force is horizontally aligned with the axis of the longitudinal force measuring device.

17. The device of claim 16, further comprising a stabilizer bar between the longitudinal force measuring device and the longitudinal pulling assembly, so that the longitudinal pulling force is transmitted to the longitudinal force measuring device through the stabilizer bar, the longitudinal pulling assembly being connected to the stabilizer bar so that the longitudinal pulling force is horizontally aligned with the axis of the of the longitudinal force measuring device.

* * * * *